United States Patent
Narula et al.

(10) Patent No.: US 8,753,654 B2
(45) Date of Patent: Jun. 17, 2014

(54) SUBSTANTIALLY ANHYDROUS COMPOSITIONS FOR PERSONAL CARE

(76) Inventors: Dipak Narula, Louisville, KY (US); Vinod K. Narula, Louisville, KY (US)

( * ) Notice: Subject to any disclaimer, the term of this patent is extended or adjusted under 35 U.S.C. 154(b) by 0 days.

(21) Appl. No.: 13/441,077

(22) Filed: Apr. 6, 2012

(65) Prior Publication Data

US 2012/0258064 A1    Oct. 11, 2012

Related U.S. Application Data

(60) Provisional application No. 61/473,413, filed on Apr. 8, 2011.

(51) Int. Cl.
| | | |
|---|---|---|
| *A61K 8/02* | (2006.01) | |
| *A61K 8/58* | (2006.01) | |
| *A61K 8/37* | (2006.01) | |
| *A61K 8/31* | (2006.01) | |
| *A61K 8/34* | (2006.01) | |
| *A61K 31/155* | (2006.01) | |
| *A61Q 19/10* | (2006.01) | |
| *A61Q 19/00* | (2006.01) | |
| *A61Q 5/00* | (2006.01) | |

(52) U.S. Cl.
CPC ........... *A61K 31/155* (2013.01); *A61K 8/585* (2013.01); *A61K 8/37* (2013.01); *A61K 8/31* (2013.01); *A61K 8/34* (2013.01); *A61Q 5/00* (2013.01); *A61Q 19/10* (2013.01); *A61Q 19/00* (2013.01)
USPC .......................................................... 424/401

(58) Field of Classification Search
None
See application file for complete search history.

(56) References Cited

U.S. PATENT DOCUMENTS

| | | | | | |
|---|---|---|---|---|---|
| 5,547,602 | A | * | 8/1996 | Schuler | .......................... 510/152 |
| 6,423,329 | B1 | * | 7/2002 | Sine et al. | ..................... 424/405 |

OTHER PUBLICATIONS

Oxiteno® Trade Paper, May 2011.*

* cited by examiner

*Primary Examiner* — Carlos Azpuru
(74) *Attorney, Agent, or Firm* — John F. Salazar; Brantley C. Shumaker; Middleton Reutlinger

(57) ABSTRACT

Moisturizers are mixtures of chemicals specifically designed to make the external layers of the skin (epidermis) softer and more pliable, by increasing its hydration (water) content and reducing evaporation. Loss of moisture in the stratum corneum causes dry skin and compromises its barrier function. Therefore, maintaining the hydration level of this layer is essential for healthy skin. For individuals who wash hands frequently or have dry skin (e.g. due to age or diabetes) using a moisturizer may be important. The personal care composition described herein provides a moisturizing system that does not have a negative effect on skin such as that which can be attributed to surfactants.

12 Claims, No Drawings

SUBSTANTIALLY ANHYDROUS COMPOSITIONS FOR PERSONAL CARE

This is a non provisional filing with the full benefit of the provisional application U.S. 61/473,413, filing date Apr. 8, 2011 as reference fully set forth.

FIELD OF INVENTION

The disclosure herein relates to compositions designed for personal care application.

BACKGROUND

An advance in moisturizing technology occurred with the development of emulsion technology and stable emulsions. An emulsion can be defined as a heterogeneous mixture that contains small droplets of immiscible or slightly miscible chemicals dispersed in another liquid. Emulsions contain lipophilic (oil soluble) or hydrophilic (water soluble) ingredients. An emulsion can be classified as oil in water (O/W) when oil droplets are stabilized by surfactants in a water continuous phase, or an emulsion can be water in oil (W/O) where the reverse is true, water droplets dispersed in a continuous liquid oil phase. Generally speaking, O/W emulsions are lower in viscosity than W/O emulsions. For moisturizers this manifests as a lotion (O/W emulsion) or a cream (W/O emulsion). Emulsifiers or surfactants are used to reduce the surface tension between the immiscible oil and water phases, with the application of shear droplets of one phase dispersed in the other.

The stability of the emulsion depends upon many variables. The size of the droplets is crucial; the smaller the droplet size, the more stable the emulsion. Formulators also use thickeners as a method to stabilize and change the esthetic feel.

Moisturizers are the most widely used cosmeceutical. Yet, the word itself is a misnomer. Moisturizers do not add water to the skin, even though the first or second ingredient on many moisturizer formulations is water. Most moisturizers function by placing a water impermeable film over the skin surface that decreases evaporation of water from the skin to the lower humidity atmosphere. Any water in a moisturizer formulation is a vehicle that evaporates, possibly drying the skin further, without enhancing water content. Water-based moisturizers may further damage xerotic skin, due to repeated wetting and drying of the skin surface.

SUMMARY

In an aspect, the invention relates to a composition comprising one or more cosmetic solvents and one or more emollients, and optionally comprising one or more natural oils, one or more occlusive agents, one or more aesthetics or feel modifiers one or more natural moisturizing factors, one or more humectants and one or more antiseptic agents.

DETAILED DESCRIPTION OF THE PREFERRED EMBODIMENTS

Certain terminology is used in the following description for convenience only and is not limiting.

The term "substantially anhydrous" with reference to a formulation herein includes but is not limited to a composition containing 25% or less water in the formulation.

The term "cosmetic solvent" with reference to a formulation herein, includes solvents suitable for use in cosmetics.

The words "a" and "one," as used in the claims and in the corresponding portions of the specification, are defined as including one or more of the referenced item unless specifically stated otherwise. This terminology includes the words above specifically mentioned, derivatives thereof, and words of similar import. The phrase "at least one" followed by a list of two or more items, such as "A, B, or C," means any individual one of A, B or C as well as any combination thereof.

Emulsifiers can cause modifications in the horny layer of human skin. Emulsifiers manipulate the integrity of the horny layers and its barrier properties of the layers; by disturbing the balance and composition of the very sensitive, so-called lipid by-layers. Emulsifiers will not lose their emulsifying properties in the skin. There are exceptions, such as low doses of soaps, which are transformed into acids like palmitic and stearic acids due to the acid milieu of the skin. These acids are also naturally present in the skin. The lasting emulsifying capacity of the emulsifiers penetrated into the skin cause an increased transport of the skin's own protective substances out of the skin, especially when the skin comes in contact with water, such as in the shower or washing hands repeatedly.

Moisturizers are mixtures of chemicals specially designed to make the external layers of the skin (epidermis) softer and more pliable, by increasing its hydration (water) content and reducing evaporation. The uppermost layer of the epidermis is the stratum corneum and is responsible for the barrier function of the skin. It is composed of dead cells held together by keratin proteins. Keratin can hold large amounts of water and prevents the skin from drying. Loss of moisture in the stratum corneum causes dry skin and compromises its barrier function. Therefore, maintaining the hydration level of this layer is essential for healthy skin.

Common moisturizers contain chemical agents that may function as humectants, occlusive agents, emollients and natural moisturizing factors.

Repeatedly washing hands with soap, which is alkaline and has a pH greater than 9, may lead to interaction between the soap and the skin, which is acidic and has a normal pH between 5 and 6. This interaction may damage the skin's barrier function. Research has found it can take several hours for the skin to regain its normal pH after a single soap and water wash. Repeated washing with soap may exasperate the condition and can lead to xerosis or dermatitis.

For individuals who wash hands frequently or have dry skin (e.g. due to age or diabetes) using a moisturizer may be important.

In an embodiment, a moisturizing system is provided that does not have a negative effect on skin such as that which can be attributed to surfactants. The basic compositions in this embodiment may contain at least one of cosmetic solvents, natural oils, emollients, occlusive agents, natural moisturizing factors, humectants, feel modifier or antiseptic agents.

An embodiment includes a composition comprising one or more cosmetic solvents and one or more emollients, and optionally comprising at least one of one or more natural oils, one or more occlusive agents, one or more natural moisturizing factors, one or more humectants, one or more aesthetics or feel modifier or one or more antiseptic agents.

An embodiment includes a personal care composition formulated for skincare. An embodiment includes a personal care composition formulated for face care. An embodiment includes a personal care composition formulated for hand care. An embodiment includes a personal care composition formulated for body care. An embodiment includes a personal care composition formulated for personal hygiene. An embodiment includes a personal care composition formulated for cleansing. An embodiment includes a personal care composition formulated for hair care.

An embodiment includes a personal care composition containing 5% to 95% of a cosmetic solvent with 1% to 95% of at least one of many natural oils, 0.5% to 95% of at least one of the many chemicals that can function as emollients, 0.1% to 95% of at least one of the many chemicals that can act as occlusive agents, 0.5% to 95% of at least one of the many chemicals that can act as humectants, 0.1% to 95% of at least one of the many chemicals that can act as a feel or aesthetics modifier and 0.1% to 95% of at least one of the many chemicals that can act as natural moisturizing factors, and may be beneficial and are suitable for use on human skin. The composition may include a cosmetic solvent having any specific percent value in the range from 1% to 95%. The composition may include a cosmetic solvent having any specific percent value between and including any two integer percent values in the range from 1% to 95%. The composition may include a natural oil having any specific percent value in the range from 1% to 95%. The composition may include a natural oil having any specific percent value between and including any two integer percent values in the range from 1% to 95%. The composition may include a chemical that can function as an emollient having any specific percent value in the range from 0.5% to 95%. The composition may include a chemical that can function as an emollient having any specific percent value between and including any two integer percent values in the range from 0.5% to 95%. The composition may include a chemical that can function as an occlusive agent having any specific percent value in the range from 0.1% to 95%. The composition may include a chemical that can function as an occlusive agent having any specific percent value between and including any two integer percent values in the range from 0.1% to 95%. The composition may include a chemical that can function as a humectant having any specific percent value in the range from 0.5% to 95%. The composition may include a chemical that can function as a humectant having any specific percent value between and including any two integer percent values in the range from 0.5% to 95%. The composition may include a chemical that can function as a feel or aesthetics modifier having any specific percent value in the range from 0.1% to 95%. The composition may include a chemical that can function as a feel or aesthetics modifier having any specific percent value between and including any two integer percent values in the range from 0.1% to 95%. The composition may include a chemical that can function as a natural moisturizing factor having any specific percent value in the range from 0.1% to 95%. The composition may include a chemical that can function as a natural moisturizing factor having any specific percent value between and including any two integer percent values in the range from 0.1% to 95%. All of the above percent values are expressed in w/w %.

In an embodiment, a personal care composition includes water. In an embodiment, a personal care composition is anhydrous. In an embodiment, a personal care composition is substantially anhydrous. A personal care composition may include 0% to 10% water content. The personal care composition may include a water content of any specific percent value in the range of 0% to 25%. The personal care composition may include a composition having a water content between and including any two specific integer percent values in the range from 0% to 10%.

In an embodiment, the personal care composition is a hand moisturizer.

In an embodiment, the personal care composition is a hand moisturizer comprising at least one of one or more cosmetic solvent, one or more natural oil, one or more emollient, one or more occlusive agent, one or more natural moisturizing factor or one or more antiseptic agent. In an embodiment, the personal care composition is a hand moisturizer comprising a cosmetic solvent, a natural oil, an emollient, an occlusive agent, a natural moisturizing factor and an antiseptic agent. The hand moisturizer may include cholesterol as a natural moisturizing factor. The hand moisturizer may include isopropyl myristate as an emollient. The hand moisturizer may include at least one of olive oil, sweet almond oil, hemp oil or coconut oil as natural oils. The hand moisturizer may include silicone fluid as a compatibilizer. The hand moisturizer may include cyclomethicone as a cosmetic solvent. The hand moisturizer may include silicone polymer as an occlusive agent. The hand moisturizer may include benzyl alcohol as an antiseptic and astringent.

In an embodiment, the personal care composition is a body wash.

In an embodiment, the personal care composition is a body wash comprising at least one of one or more cosmetic solvent, one or more natural oil, one or more compatibilizer, one or more emollient, one or more occlusive agent, one or more analgesic or one or more antiseptic agent. In an embodiment, the personal care composition is a body wash comprising a cosmetic solvent, a natural oil, a compatibilizer, an emollient, an occlusive agent, an analgesic and an antiseptic agent. The body wash may include cyclomethicone as a cosmetic solvent. The body wash may include at least one of coconut oil, sweet almond oil or olive oil as a natural oil. The body wash may include silicone fluid as a compatibilizer. The body wash may include isopropyl myristate as an emollient. The body wash may include silicone polymer as an occlusive agent. The body wash may include isopropyl alcohol as a solvent and antiseptic agent. The body wash may include benzyl alcohol as an analgesic. The body wash may include parachlorometaxylenol as an antiseptic agent.

In an embodiment, the body wash aids patients with dementia or other ailments that make the patients adverse to a wet feel or cooling sensation produced when water evaporates from the skin. This may be accomplished by preparing a personal care composition with a proper heat of evaporation.

In an embodiment, the body wash is suited for outdoor activities where the availability of water and facilities is limited.

In an embodiment, the body wash is suited for military in field use.

In an embodiment, the personal care composition is a facial cleanser.

In an embodiment, the personal care composition is a facial cleanser comprising at least one of one or more cosmetic solvent, one or more emollient, one or more humectant, one or more moisturizer, one or more anti-inflammatory, one of more skin conditioning agent, one or more antioxidant or one or more analgesic. In an embodiment, the personal care composition is a facial cleanser comprising a cosmetic solvent, an emollient, a humectant, a moisturizer, an anti-inflammatory, a skin conditioning agent, an antioxidant and an analgesic. The facial cleanser may include cyclomethicone and/or dodecane as a cosmetic solvent. The facial cleanser may include caprylyl glycol as an emollient and humectant. The facial cleanser may include *Cucumis Sativus* (cucumber) as an anti-inflammatory and a moisturizer. The facial cleanser may include Aloe barbadensis leaf juice as an emollient. The facial cleanser may include tocopheryl acetate as an antioxidant and skin conditioning agent. The facial cleanser may include benzyl alcohol as an analgesic.

In an embodiment, the strength of the personal care composition may be changed by increasing ingredients or adding further ingredients to meet various markets such as consumer, medical or institutional.

In an embodiment, the personal care composition is a hair oil comprising at least one of one or more cosmetic solvent, one or more shine enhancing, one or more compatibilizer, one or more moisturizer, one or more anti-inflammatory, one of more hair conditioning agent or one or more analgesic. In an embodiment, the personal care composition is a hair oil comprising a cosmetic solvent, shine enhancing, a compatibilizer, an anti-inflammatory, a hair conditioning agent, an antioxidant and an analgesic. The facial cleanser may include cyclomethicone and/or dodecane as a cosmetic solvent. The facial cleanser may include phenyl trimethicone as a shine enhancer. The hail oil may include capryl methicone as a combatibilizer. The facial cleanser may include almond oil as a moisturizer. The hair oil may include tocopheryl acetate as an antioxidant. The hair oil may include benzyl alcohol as an analgesic)).

In an embodiment the personal care composition is for hand hygiene comprising a solvent, emollients, humectants, feel modifiers and an antiseptic agent. The hand hygiene composition may contain low molecular weight alcohols like ethanol, isopropyl alcohol or n-propyl alcohol.

In an embodiment, the personal care composition contains natural oils that coordinate with, approach or match the chemical composition of skin. In an embodiment, the personal care composition contains four natural oils that match the chemical composition of skin. In an embodiment, the personal care composition contains hemp oil, sweet almond oil, olive oil and coconut oil that match the chemical composition of skin. The approximate chemical composition of skin lipids is: 50% ceramides, 25% cholesterol and 15% fatty acids. Table I illustrates the fatty acid content of the skin compared to the fatty acid composition of the four natural oils.

TABLE I

| Fatty Acid Content | alpha Linolenic Acid | Linolenic Acid | Oleic Acid | Steric Acid | Palmitic Acid |
|---|---|---|---|---|---|
| Skin* | | 7.3 | 45.6 | 22.0 | 40.0 |
| Hemp Oil** | 20.0 | 60.0 | 12.0 | 2.0 | 6.0 |
| Sweet Almond Oil** | | 17.0 | 78.0 | 5.0 | |
| Olive Oil** | | 8.0 | 75.0 | 16.0 | |
| Coconut Oil** | | 3.0 | 6.0 | | 91.0 |

*Skin composition expressed in percent, based on extraction data.
**Composition of oils is w/w %.

In an embodiment, the personal care composition is a spray application.

In an embodiment, any personal care composition herein contains a natural moisturizing factor comprising cholesterol.

In an embodiment, a personal care composition is formulated to meet the needs of people who wash their hands frequently.

In an embodiment, a personal care composition soothes dry itchy skin caused by frequent hand washing with soap and water.

In an embodiment, a personal care composition is free of any color dyes, fragrances, emulsifiers and thickeners.

EXAMPLE 1

Formulation for a Hand Moisturizer—Table II

TABLE II

| | | Wt % |
|---|---|---|
| Cholesterol | Natural moisturizing factor | 0.09 |
| Isopropyl Myristate | Emollient | 1.70 |
| Olive Oil | Natural oil | 2.55 |
| Sweet Almond Oil | Natural oil | 2.55 |
| Hemp Oil | Natural oil | 0.85 |
| Coconut Oil | Natural oil | 2.55 |
| Silicone fluid | As a compatibilizer, feel modifier | 3.40 |
| Cyclomethicone | Solvent | 85.03 |
| Silicone polymer | Occlusive agent | 0.85 |
| Benzyl Alcohol | Antiseptic and astringent | 0.43 |

The example is shown as an illustration, other such formulation can be developed by one skilled in the art. Other Natural moisturizing factors that are compatible within the composition can be selected for an extensive list of such chemicals. Similarly, other emollients, natural oils, compatibilizing agents, occlusive agents, antiseptic, astringents and solvents can be selected depending on the desired function and properties of the final formulation. In an embodiment of a hand moisturizing composition contains; a natural moisturizing factor in the range of 0.01% wt to 15% wt, emollients in the range of 0.01% wt to 20.0% wt, natural oils in the range of 1.0% to 50% wt, compatibilizing agents in the range of 0.1% wt to 25% wt, occlusive agents in the range of 0.1% wt to 20.0% wt, antiseptic agents in the range of 0.01% to 15.0% wt, astringents in the range of 0.01% to 10.0% wt and solvent in the range of 1.0% to 95.0% wt. In an embodiment the solvents can range from 5.0% to 90.0% wt. In an embodiment the solvent can range from 10.0% to 80.0% wt.

EXAMPLE 2

Formulation for a Body Wash—Table III

TABLE III

| | | Wt % |
|---|---|---|
| Cyclomethicone | Solvent | 77.15 |
| Coconut oil | Natural oil | 0.50 |
| Sweet Almond Oil | Natural oil | 0.50 |
| Olive Oil | Natural oil | 0.50 |
| Silicone fluid | As a compatibilizer, feel modifier | 0.50 |
| Isopropyl Myristate | Emollient | 0.25 |
| Silicone polymer | Occlusive agent | 0.10 |
| Isopropyl Alcohol | Solvent | 20.0 |
| Benzyl Alcohol | Analgesic | 0.25 |
| Parachlorometaxylenol | Antiseptic agent | 0.25 |

In an embodiment a body wash would contain; natural oils in the range of 0.5% wt to 25.0% wt, emollients in the range of 0.01% wt to 15.0% wt, occlusive agents in the range of 0.01% wt to 10.0% wt, antiseptic agents and or analgesic in the range 0.01% wt to 10.0% wt and one or more solvents in the range of 1.0 wt % to 99.0% wt. In an embodiment the solvents can range from 5.0% to 90.0% wt. In an embodiment the solvent can range from 10.0% to 80.0% wt. In an embodiment other chemicals beneficial for skin care such as astringents, antioxidants, natural moisturizing factors, and humectants may be added along with fragrance.

EXAMPLE 3

Formulation for a Facial Cleanser—Table IV

TABLE IV

|  |  | Wt % |
|---|---|---|
| Cyclomethicone | Solvent | 83.1 |
| Dodecane | Solvent | 10.0 |
| Almond Oil | Natural oil | 0.5 |
| Capryl methicone | Cleanser | 1.5 |
| Caprylyl Glycol | Emollient, humectants | 1.0 |
| *Cucumis Sativus* (cucumber) | Moisturizer, anti-inflammatory | 0.75 |
| *Aloe barbadensis* leaf juice | Emollient | 1.5 |
| Tocopheryl acetate | Antioxidant, skin conditioning agent | 1.5 |
| Benzyl Alcohol | Analgesic | 0.15 |

In an embodiment of a cleanser that can be use on the face, eyes and general cleaning of skin, may contain analgesic, antioxidant, skin conditioning, anti-inflammatory agents ranging from 0.1% wt to 15.0% wt, emollients, humectants, moisturizing agents in the range of 0.1% wt to 20.0% wt, natural oils, cleansing agents in the form of silicones, alcohols or other compounds in the range of 0.1 to 20.0% wt and one or more solvents in the range of 1.0% to 95.0% wt. In an embodiment the solvents can range from 5.0% to 90.0% wt. In an embodiment the solvent can range from 10.0% to 80.0% wt. In an embodiment other cosmetically acceptable ingredients such as fragrance may be added.

EXAMPLE 4

Formulation for a Hair Oil—Table V

TABLE V

|  |  | Wt % |
|---|---|---|
| Cyclomethicone | Solvent | 90.50 |
| Phenyl trimethicone | Shine enhancing agent | 5.0 |
| Capryl methicone | Compatibilizer | 2.75 |
| Almond oil | Natural oil | 0.5 |
| Tocopheryl acetate | Antioxidant | 1.0 |
| Benzyl Alcohol | Analgesic | 0.25 |

In an embodiment of a hair oil may contain agents that impart gloss or shine to hair in the range of 0.01% to 25.0% wt. In an embodiment may contain compatibilizing agents in the range of 0.01% to 25.0% wt. In an embodiment may contain natural oils in the range of 0.01% to 25.0% wt. In an embodiment may contain antioxidant in the range of 0.01% to 10.0% wt. In an embodiment may contain analgesic in the range of 0.01% wt to 10.0% wt. In an embodiment solvent can range from 1.0% to 95.0% wt. In an embodiment the solvents can range from 5.0% to 90.0% wt. In an embodiment the solvent can range from 10.0% to 80.0% wt. In an embodiment may contain other ingredients such as hair dye, hair color, ultra violet blockers and fragrance.

EXAMPLE 5

Formulation for Hand Hygiene—Table VI

TABLE VI

|  |  | Wt % |
|---|---|---|
| Ethyl Alcohol | Solvent | 70.00 |
| Isoproply Myristate | Emollient | 0.25 |
| 1,3,propanediol | Humectant | 4.00 |
| Cyclopentacone | Feel modifier | 2.00 |
| Chlorhexidine digluconate 20% solution | Antiseptic agent | 10.00 |
| Water | Solvent | 13.75 |

In an embodiment of a hand hygiene composition may contain an emollient in the range of 0.01% to 15.0% wt. In an embodiment may contain humectant in the range of 0.01% to 20.0% wt. In an embodiment may contain feel modifier in the range of 0.01% to 10.0% wt. In an embodiment may contain antiseptic agents in the range of 0.01% wt to 25% wt. In an embodiment solvent can range from 1.0% to 95.0 wt %. In an embodiment the solvents can range from 5.0% to 90.0% wt. In an embodiment the solvent can range from 10.0% to 80.0% wt.

It is understood, therefore, that this invention is not limited to the particular embodiments disclosed, but is intended to cover all modifications which are within the spirit and scope of the invention as defined by the appended claims; and/or the above description.

What is claimed is:
1. A personal care composition comprising:
   one or more cosmetic solvents in a range of 1.0% to 99.0%;
   one or more emollients in a range of 0.01% to 15.0%;
   less than about 10% of an antiseptic agent; and
   one or more of a natural oil in a range of 0.5% to 25.0%, an occlusive agent in a range of 0.01% to 10.0%, a natural moisturizing factor, and a humectant;
   wherein the composition is substantially anhydrous and is in a form that is applicable as a spray.
2. The personal care composition of claim 1, wherein the composition is formulated for skincare, face, hand and body, personal hygiene, cleansing and hair care.
3. The personal care composition of claim 1, wherein the cosmetic solvent is cyclomethicone.
4. The personal care composition of claim 1, wherein the composition is a hand moisturizer.
5. The personal care composition of claim 1, wherein the composition is a body wash.
6. The personal care composition of claim 1, wherein the composition is a facial cleanser.
7. The personal care composition of claim 1, wherein the composition is a hair oil.
8. The personal care composition of claim 1, wherein the composition is used for hand hygiene.
9. The personal care composition of claim 1, wherein the composition is a spray application.
10. The personal care composition of claim 1, wherein the natural moisturizing factor is cholesterol.
11. The personal care composition of claim 1, wherein:
   the one or more cosmetic solvents comprise Ethyl Alcohol and water;
   the one or more emollients comprise Isoproply Myristate;

the antiseptic agent comprises Chlorhexidine digluconate; and the personal care composition further comprises 1,3,propanediol and Cyclopentacone.

12. The personal care composition of claim 1, wherein:

the one or more cosmetic solvents comprise cyclomethicone and dodecane;

the one or more emollients comprise caprylyl glycol and aloe babadensis leaf juice; and the personal care composition further comprises almond oil, capryl methicone, cucumis sativusm tocopheryl acetate and benzyl alcohol.

* * * * *